United States Patent [19]

Ragland

[11] Patent Number: 4,744,984

[45] Date of Patent: May 17, 1988

[54] ANTIVIRAL IMMUNOTHERAPEUTIC AGENT AND PREPARATION THEREOF

[75] Inventor: William L. Ragland, Athens, Ga.

[73] Assignee: Vetrepharm Research, Inc., Athens, Ga.

[21] Appl. No.: 785,070

[22] Filed: Oct. 8, 1985

[51] Int. Cl.$^4$ ...................... A61K 39/02; A61K 35/78
[52] U.S. Cl. .................................. 424/92; 424/195.1; 514/885; 514/937; 514/938
[58] Field of Search ............... 424/92, 195.1; 514/885, 514/937, 938

[56] References Cited

U.S. PATENT DOCUMENTS

| | | | |
|---|---|---|---|
| 3,331,741 | 7/1967 | Anschel et al. | 424/92 |
| 4,069,314 | 1/1978 | Adlam et al. | 424/92 |
| 4,340,586 | 7/1982 | Bekierkunst et al. | 424/92 |
| 4,503,048 | 3/1985 | Cartrell | 424/195.1 |
| 4,504,473 | 3/1985 | Cartrell | 424/92 |
| 4,505,903 | 3/1985 | Cartrell | 424/195.1 |
| 4,520,019 | 5/1985 | Ribi et al. | 424/195.1 |

OTHER PUBLICATIONS

Regression of Tumors in Guinea Pigs After Treatment with Synthetic Muramyl Dipeptides and Trehalose Dimycolate, Science, vol. 208, pp. 415–416, 1980, Charles A. McLaughlin, Steven M. Schwartzman, etc.
In Vitro Effects of Lipopolysaccharides and Mycobacterial Cell Wall Components on Swine Alveolar Macrophages, Research in Veterinary Science, pp. 212–217, vol. 34, 1983, B. Charley, C. Leclerc, E. Petit, L. Chedid.
Synthetic Immunostimulants Derived from the Bacterial Cell Wall, Journal of Medicinal Chemistry, vol. 23, No. 8, pp. 819–821, 1980, Edgar Lederer.
Immunologic Effects of BCG in Patients with Malignant Melanoma: Specific Evidence for Stimulation of the "Secondary" Immune Response, Journal of the National Cancer Institute, vol. 51, No. 1, pp. 57–65, 1973, Leonard Chess, M.D., Gerald N. Bock, M.D., etc.
BCG and Cancer, New England Journal of Medicine, vol. 290, Nos. 25 and 26, pp. 1413–1420 and 1458–1469, 1974, Robert C. Bast, Jr., M.D., Berton Zbar, M.D., etc.
Enhancement of Nonspecific Immunity to Klebsiella Pneumoniae Infection by a Synthetic Immunoadjuvant (N-acetylmuramyl-L-alanyl-D-isoglutamine) and Several Analogs, Proceedings of the National Academy of Science U.S.A., Vol. 74, pp. 2089–2093, 1977, L. Chedid, M. Parant, etc.
The Activation of Human Monocytes by Liposome—Encapsulated Muramyl Dipeptide Analogues, The Journal of Immunology, vol. 133, No. 4, pp. 1500–1502, 1983, Gabriel Lopez-Berestein, Kapil Mehta, etc.
Human Monocytes Activated by Immunomodulators in Liposomes Lyse Herpesvirus-Infected but Not Normal Cells, Science, vol. 224, pp. 1007–1009, Wayne C. Koff, Isaiah J. Fidler, etc.

*Primary Examiner*—John Rollins
*Attorney, Agent, or Firm*—Jones, Askew & Lunsford

[57] ABSTRACT

The present invention relates to an immunotherapeutic agent that is effective in treating a wide variety of ongoing viral infections in animals and man. The present invention is a preparation of modified mycobacterial cell walls that is capable of stimulating the immune system of an animal or man in such a way as to cause the body to neutralize, abort or eliminate an virus infection.

3 Claims, No Drawings

ANTIVIRAL IMMUNOTHERAPEUTIC AGENT AND PREPARATION THEREOF

TECHNICAL FIELD

The present invention relates to an immunotherapeutic agent that is effective in treating ongoing viral infections in animals and man. More particularly, the present invention is a preparation of modified mycobacterial cell walls that is capable of stimulating the immune system of an animal or man in such a way as to cause the body to neutralize, abort or eliminate a virus infection.

BACKGROUND OF THE INVENTION

As used herein, the term "virus" refers to a simple infectious organism that is an obligatory intracellular parasite. The term "virus particle" is a bloc of genetic material (either DNA or RNA) capable of autonomous replication, surrounded by a protein coat and sometimes by an additional membranous envelope which protects the virus particle from the environment and serves as a vehicle for its transmission from one host cell to another. The term "host" is an animal or human which is infected by a specific type of virus. The term "host cell" is a cell that is infected by a virus particle.

Viral infections are difficult to treat in animals and man due to the unique manner in which viruses utililize a host's own metabolic machinery to replicate new virus particles. Unlike cells, viruses do not grow in size and then divide because they contain within their coats few or none of the biosynthetic enzymes and other machinery required for their replication. Rather, viruses replicate in host cells by synthesis of their separate components and then assembly of the individual components. Thus, the viral nucleic acid, after shedding its coat, comes in contact with the appropriate cell machinery. The viral nucleic acid then specifies the synthesis of proteins required for viral reproduction. The viral nucleic acid is itself replicated, through the use of both viral and host cell enzymes; the components of the viral coat are synthesized; and these two components are then assembled to form a complete virus particle, also called a virion.

Because viruses use a host cell's enzymatic machinery to replicate, viral infections cannot be treated as infections caused by cellular microorganisms. Chemicals that will block the replication of viruses will also block the enzymes that are required for a host cell to live, thereby damaging or killing the host cell. For this reason, virus infections cannot be treated using conventional antimicrobial drugs.

Viruses are subdivided into three main classes; animal viruses, bacterial viruses, and plant viruses. Within each class, each virus is able to infect only cells from certain species. The host range is determined by the specificity of attachment to the cells. This depends on properties of both the virus' coat and specific receptors on the host cell's surface.

Most viruses that naturally infect a particular species of animal will usually be controlled by the animal's immune system. After a virus infects an animal, the animal's immune system will eventually recognize the presence of the virus and be stimulated to remove or neutralize the infecting viral particles. One of the problems with the natural system is that it takes the immune system time to recognize the virus and to become sufficiently stimulated so as to effectively remove the virus from the system. During the time that the immune system is being stimulated, the infecting virus can cause great damage. For example, viral infections may cause damage to vital tissues, such as brain, nerves, liver, etc. The crippling sequelae of poliomyelitis virus infections of humans, the muscle tics which follow distemper infections of dogs, and fibrosis and cirrhosis of the liver subsequent to viral hepatitis in humans, are but examples of permanent injury which may be caused by viral infections before the immune system has had sufficient time to develop an adequate response. Death frequently occurs in fulminating infections before the immune system can respond to the infectious agent.

Viral infections commonly compromise a host's defenses to other organisms, especially opportunistic bacteria, with a result that many of the signs and symptoms characteristic of many diseases are actually caused by these secondary invaders. A classic example of this type of secondary infection is bacterial infection which follows viral infection of respiratory tissues. Furthermore, other signs and symptoms of many viral infections are caused by inflammatory and toxic factors released by infected cells and cells which have died subsequent to viral infection. Multiple replicatory cycles of viral propagations usually are necessary to produce sufficient amounts of these factors to significantly affect a host.

Conventional therapy for preventing future viral infections includes immunization against a particular virus. Immunization against a virus requires the introduction of either live, attenuated (inactivated) virus or dead virus particles into the body. The body will recognize the virus and mount a specific immune response against the virus. After immunization against the virus, the immune system of the body will readily attack and neutralize an invading virus because the body has been previously primed by the inactivated or killed virus and will "remember" that particular virus. However, the protection is only effective against the virus to which the body had been immunized. Effective protection by immunization usually requires at least two to four weeks. Often, a second or even third "booster" shot will be required to maintain maximum immunization. Although immunization provides long term protection against future infection by a virus, immunization is ineffective against current, ongoing infections. Immunization is also only effective against the virus that was used to immunize the animal.

Thus, what is needed is a therapeutic agent that is capable of rapidly stimulating the immune system, in vivo, in such a way as to cause the immune system of the host animal to neutralize the virus, or interrupt its replication by recognizing and killing infected cells so that it can no longer infect other host cells.

SUMMARY OF THE INVENTION

The present invention solves the above problems by providing an immunotherapeutic agent that can be administered to an animal that has been infected with a virus and will cause the immune system of the infected animal to be generally stimulated. This stimulation of the immune system causes the infecting virus to be rapidly neutralized. Administration of the antiviral immunotherapeutic agent of the present invention causes the immune system to be generally stimulated. The stimulated immune system is then capable of rapidly neutralizing an infecting virus. When a viral infection is aborted by use of the antiviral immunotherapeutic of the present invention, the signs and symptoms produced by viral replication and secondary bacterial infections are considerably reduced or inapparent because interruption of viral replication breaks the infective cycle.

The antiviral immunotherapeutic agent of the present invention comprises a modified cell wall fraction from Mycobacterium species. Briefly, the bacteria are grown in liquid medium and harvested. The cell walls are prepared by disrupting the bacteria and then harvesting the disrupted bacteria by centrifugal sedimentation. The cell wall fraction (pellet from the centrifugation step) is then deproteinized by digestion with proteolytic enzymes. The resulting fraction is then treated with detergents and washed. The resulting insoluble fraction is then lyophilized. This fraction can be adsorbed to lipid droplets which are suspended in an appropriate adjuvant/stabilizer and injected into an animal or human to abort a viral infection.

The resulting deproteinized cell wall fraction can be used to treat a wide variety of viral infections including, but not limited to, infection by herpesvirus such as equine rhinopneumonitis, infectious bovine rhinotracheitis, herpes simplex, and a herpesvirus which infects urinary tracts of cats. The invention also is effective as an aid in the treatment of parvovirus infections of young dogs. The antiviral immunotherapeutic of the present invention is efficacious as a therapeutic for genital herpes infections and acquired immune deficiency syndrome of man, as well as other viral infections of animals and man.

The antiviral immunotherapeutic agent of the present invention is different from conventional therapy in that the present invention nonspecifically causes the immune system to be activated, thereby providing protection against a wide variety of viral infections. Thus, the present invention is effective in treating viral infections in animals that are not immune to the infecting virus.

Accordingly, it is an object of the present invention to provide an antiviral immunotherapeutic that is effective in treating an animal or human that is infected with a virus.

It is a further object of the present invention to provide an antiviral immunotherapeutic agent that is effective in treating a wide variety of viral infections.

Another object of the present invention is to provide an antiviral immunotherapeutic agent that is non-toxic to the recipient.

Another object of the present invention is to provide an antiviral immunotherapeutic agent that will rapidly cure an animal or human of a viral infection.

Another object of the present invention is to provide an antiviral immunotherapeutic agent that does not sensitize the host to tuberculin skin tests.

Yet another object of the present invention is to provide an antiviral immunotherapeutic agent that is effective in treating an ongoing viral infection.

Another object of the present invention is to provide an antiviral immunotherapeutic agent that can be stored for a long period of time and remain effective.

Another object of the present invention is to provide an antiviral immunotherapeutic agent that will not cause anaphylaxis.

These and other objects, features and advantages of the present invention will become apparent after a review of the following detailed description of the disclosed embodiment and the appended claims.

DETAILED DESCRIPTION OF THE DISCLOSED EMBODIMENT

The present invention relates an immunotherapeutic agent that is effective in treating virus infections in animals and man. The present invention is a preparation of modified bacterial cell walls that is capable of stimulating the immune system of an animal or man in such a way as to cause the body to neutralize or abort a viral infection.

The present invention does not cause a positive tuberculine reaction in the recipient and rarely causes an anaphylactic response upon repeated injection. The antiviral immunotherapeutic agent of the present invention can be used to treat a wide variety of viral infections including infections caused by herpesviruses. It is to be understood that the present invention is not an immunization process but is an agent that is capable of generally stimulating the immune system of an animal or human so that the individual's own immune system is capable of rapidly eliminating the viral infection. Thus, the antiviral immunotherapeutic agent of the present invention is ideally suited for treatment of ongoing viral infections and is a novel immunotherapeutic agent in contrast to conventional prophylactic immunization.

The antiviral immunotherapeutic agent of the present invention comprises a modified bacterial cell wall preparation. The preferred microorganism is the *Mycobacterium phlei*. However, any Mycobacterium species can be used to prepare the antiviral immunotherapeutic agent of the present invention. Other bacteria that can be used as a source of cell walls are Corynebacterium species and Nocardia species.

Basically, the antiviral immunotherapeutic agent of the present invention is prepared by growing the *Mycobacterium phlei* in Bacto AC broth (Difco Labs, Detroit, MI) for 10 to 20 days after primary culture on Petragnani medium (Difco Labs, Detroit, MI) or in Lowenstein-Jensen medium (Difco Labs, Detroit, MI) for 10 to 20 days. The cells are harvested by centrifugal sedimentation and disrupted either under pressure or by sonic disruption. Disruption of bacteria means breaking the bacterial cell walls so that the soluble contents of the bacteria are released into the surrounding environment. The disrupted bacterial cells are collected by centrifugation and resuspended in distilled water. The cell/water suspension is first treated in a blender at high speed. The cells are further disrupted in a high pressure cell fractionator such as a Ribi Cell Fractionator. This particular cell fractionator is no longer manufactured but is well known to one of ordinary skill in the art. The bacterial cells are placed in a chamber. The chamber is then pressurized to pressures greater than 30,000 pounds per square inch. The pressure is then rapidly released and the cells are disrupted by decompression. The bacterial cells may also be disrupted by sonication in a sonifer such as a Branson Sonifier 350 cell disruptor (Branson Sonic Power Co., Danbury, CT).

The cell wall fraction is then washed and separated from any unbroken cells. The effluent or sonicate is transferred to centrifuge bottles and is spun at about $27,500 \times g$ for 1 hour at 15° C. in an intermediate speed centrifuge. After centrifugation, the supernatant solution is discarded and the sedimented crude cell wall fraction is transferred to a blender. It is important at this step to discard the undermost, white pellet of unbroken cells. The cell walls are suspended in deionized, sterile water and are washed by centrifugation. The washed cell wall fraction is resuspended in deionized, sterile water and spun at low speed (about 350 to 500×g) to remove any unbroken cells. After the low speed centrifugation, the cell wall fraction is pelleted from the supernatant solution by centrifugation at 27,500×g.

The crude cell wall fraction is then deproteinized by treating the cell walls with several proteinases. It is to be understood that many different proteinases, and even chemical extraction methods, can be used for this step in the cell wall modification process. The preferred method of deporteinating the cell walls is by sequential treatment of the cell wall fraction with trypsin and pronase. The crude cell wall fraction is resuspended in an aqueous buffered solution such as 0.05M Tris-HCl, pH 7.5. Trypsin (pancreatic trypsin, Sigma Chemical Co., St. Louis, MO) is added and the mixture is stirred at room temperature for 6 to 24 hours. After the trypsin treatment, pronase (*Streptomyces griseus* protease, Sigma Chemical Co., St. Louis, MO) is added and the suspension is allowed to incubate at room temperature for 6 to 24 hours.

The cell wall fraction is then optionally treated with detergent and phenol to extract any nucleic acids and/or lipids that may be present in the cell wall fraction. The preferred mixture is urea, Triton X-100 and phenol. For example, between about 40 to 80 g of urea, 0.5 to 4 ml of 100% Triton X-100, and 50 to 150 g of phenol are added to each liter of deproteinized cell wall suspension. The suspension is then warmed to about 60° to 80° C. and stirred for 1 hour. After the heating step with the phenol and detergents, the suspension is spun for 10 minutes at about 16,000×g in capped bottles in an intermediate speed centrifuge in a GSA rotor. The supernatant solution is decanted and the dark phenol solution under the pellet is carefully removed. The cell wall pellet is washed several more times by centrifugation to remove any residual phenol.

Next the modified cell wall pellet is lyophilized, a process well known to one of ordinary skill in the art. The lyophilized cell wall pellet can be stored indefinitely at −20° C. in a desiccator jar.

The antiviral immunotherapeutic agent of the present invention is emulsified in an adjuvant before use. The adjuvant can be any one of many adjuvants that are well known to one skilled in the art. The preferred adjuvant is an oil and water emulsion. The antiviral immunotherapeutic agent of the present invention is mixed with the oil before aqueous buffer with detergent is added. The mixture is then emulsified by any one of several methods. These methods include homogenization using a high speed blender, sonication, or a Potter-Elvehjem homogenizer.

It is to be understood that the method of preparing the emulsion is not critical. Numerous variations of the compositions of the aqueous and oil phases, their proportions and means of emulsification will be apparent to those of ordinary skill in the art and could be used with the antiviral immunotherapeutic agent in practicing the present invention.

The preferred emulsions of deproteinized cell walls are prepared by addition of between approximately 5 and 15 g of dry, deproteinized mycobacterial cell wall to a dry, one liter beaker. Mineral oil (Drakeol 6-VR, Penreco, Butler, PA), squalene, or the synthetic mineral oil n-hexadecane) is added at between approximately 10 and 50 ml per gram of cell walls. The suspension is covered and is mixed for approximately 30 minutes to overnight. Approximately 10 ml aliquots of the oil/cell wall mixture are transferred to 1 liter beakers. To each aliquot is added 500 ml of sterile phosphate buffered saline (PBS). The mixture is homogenized by sonication and transferred to sterile, bottles and stored at 4° C.

Aluminum hyroxide stabilizer may be optionally added to the modified cell wall emulsion. Aluminum hydroxide is obtained as a 9.4% compressed gel from the Reheis Chemical Co. (Berkeley Heights, NJ) and is hydrated to 1.3% aluminum oxide by the addition of deionized water. The gel is sterilized in an autoclave at 120° C. for 20 minutes before it is added to the cell wall emulsion. One liter of the final emulsion contains about 900 ml of emulsified cell walls, 50 ml of 1.3% aluminum oxide, and 40 ml of added PBS. Thimerosal (ethylmercurithiosalicylate, Sigma Chemical Co., St. Louis, MO) can optionally be added as a preservative. The preferred concentration of Thimerosal is about 0.1 g per liter. The aluminum oxide, Thimerosal and additional buffer are optionally added to the emulsified cell walls prior to the step of mixing at 60°-80° C. for one hour.

The antiviral immunotherapeutic agent of the present invention is used preferably by injecting a single dose of the agent intramuscularly. However, it should be understood that the present invention is effective when injected subcutaneously or intravenously. For some diseases, more than one treatment may be desirable. The optimal dose of the antiviral immunotherapeutic agent of the present invention varies slightly with the size of the animal that is being treated. Only an amount sufficient to stimulate the immune system is required. Normally a single dose is an emulsion of from about 0.1 to 4.0 mg of cell wall per ml in a total volume of from about 0.25 to 5.0 ml.

The known active ingredients of the present invention, i.e., the family of muramyl dipeptides and trehalose dimycolate, as well as any unknown active components which may be present in the deproteinized cell wall skeletons of bacteria may be delivered to the hose by any of a number of vehicles other than the preferred oil in water emulsions. The present invention can be used with any one, all, or any combination of ingredients regardless of the carrier/vehicle used to present them to the responsive immune cells; carriers such as liposomes, various biodegradable or nondegradable polymers, osmotic minipumps, etc.

The following examples will serve to further illustrate the present invention without, at the same time, however, constituting any limitation thereof.

EXAMPLE I

*Mycobacterium phlei* was obtained from the Institut fur Experimental Biologie and Medizin, Borstel, West Germany, and was stored as a suspension in sterile milk at −60° C. Approximately 11 transfers of the isolate were made between 1976 and 1985 without any diminution of antiviral activity of the modified cell walls. The *M. phlei* was cultured on Petragnani medium (Difco Labs, Detroit, MI).

EXAMPLE II

Bacterial cell walls were prepared with a Ribi Cell Fractionator. The Ribi cylinder, piston, and valve components were cleaned and assembled before each use. Approximately 400 grams of moist cell mass were placed into a clean blender with a capacity of approximately 1200 ml. The cell mass was mixed at high speed for between 30 to 60 seconds. After mixing, 6 ml of Tween 80 and between 200 and 400 ml of sterile water were added to the cell mixture. The entire cell suspension was then mixed in the blender at low speed for about 10 seconds. The cell suspension was refrigerated and remixed before each refill of the Ribi cylinder.

The Ribi cylinder was filled with the cell suspension and processed in the fractionator at 33,000 pounds per square inch. The cylinder was then refilled and the procedure was repeated until the entire cell suspension had been processed. The effluent from the Ribi cylinder was stored in a sterile flask on ice during the fractionation process.

EXAMPLE III

The effluent from the fractionation procedure of Example II was transferred to 250 ml centrifuge bottles and spun for 1 hour at 27,500×g at 15° C. in an intermediate speed centrifuge with a GSA rotor. The supernatant fluid from the centrifugation was then decanted and discarded. The undermost, white pellet of unbroken cells was discarded. The sedimented crude cell wall fraction was transferred to a blender and suspended in sterile, deionized water by mixing at low speed. The crude cell wall fraction was washed by resuspension and centrifugation (27,500×g at 15° C. for one hour). Again, the undermost, white pellet of unbroken cells was discarded.

After washing the crude cell wall fraction, the pellet was resuspended in sterile, deionized water and spun for 5 minutes at 350×g to sediment unbroken cells while retaining the cell walls in the supernatant fluid. The supernatant fluid was then decanted and centrifuged at 27,500×g for 1 hour at 15° C. to sediment the crude cell wall fraction.

EXAMPLE IV

The crude cell wall fraction from Example III was then deproteinized by digestion with proteolytic enzymes. The crude cell wall fraction derived from about 400 g of whole cells was resuspended in 1 liter of 0.05M Tris-HCl, pH 7.5, by mixing at low speed. After the crude cell wall fraction was thoroughly resuspended in the Tris buffer, 50 mg of trypsin (pancreatic trypsin, Sigma Chemical Co., St. Louis, MO) were added and stirred using a magnetic stirring bar at room temperature for 24 hours. Following the trypsin treatment, 50 mg of pronase (*Streptomyces griseus* protease, Sigma Chemical Co., St. Louis, MO) were added to each liter of trypsin digested cell wall suspension. The suspension was stirred using a magnetic stirring bar for 24 hours at room temperature.

EXAMPLE V

The protease digested cell wall fraction from Example IV was then treated with detergent and phenol. To each liter of cell wall suspension, 60 g of urea (J. T. Baker Chemical Co., Phillipsburg, NJ), 2.0 ml of 100% Triton X-100 (polyoxyethylene ethers, Sigma Chemical Co., St. Louis, MO), and 100 g of phenol crystals (Fisher Scientific, Fair Lawn, NJ) was added. The flask containing the suspension was loosely covered with aluminum foil and warmed to 60°-80° C. and stirred for one hour. The deproteinized cell wall fraction was then spun for 10 minutes at 16,000×g in a GSA Rotor (Ivan Sorvall, Inc., Norwalk, CT). The supernatant fraction was decanted and discarded and the dark fluid beneath the pellet was removed using a disposable pipet. The cell wall pellet was washed three times by resuspending it in about one liter of sterile water, and centrifuged at 16,000×g for 10 minutes in a GSA rotor.

EXAMPLE VI

The washed, modified cell wall pellet was then lyophilized by transferring the suspension to a lyophilizing flask with a small amount of deionized sterile water. One 300 ml lyophilizing flask was used for each 30 grams of wet cell wall starting material. The cell wall suspension was shell frozen by rotating the flask in ethanol that had been cooled with solid carbon dioxide. After the content of the flask was frozen, the flask was attached to a lyophilization apparatus (Virtis Co., Inc., Gardiner, NY). After the sample was lyophilized, it was transferred to a sterile, screw-cap container. The material was stored at −12° C. in a desiccator jar containing anhydrous calcium sulphate.

EXAMPLE VII

Emulsions of deproteinized cell walls were prepared in 4 steps: (1) addition of dry, deproteinized, mycobacterial cell wall and mineral oil (Drakeol 6-VR) to an emulsification vessel, (2) suspension of the cell wall in the oil, (3) addition of buffered saline solution containing a detergent to the mixture of cell wall and oil, and (4) emulsification of the oil-cell wall complex into the aqueous detergent saline solution.

The emulsification was accomplished by sonication using a Branson Sonifier 350 cell disruptor. Several grams of lyophilized, deproteinized cell wall fraction were added to a dry, sterile, one liter beaker. Mineral oil was added at a concentration of 20 ml per g and the mixture was covered and allowed to sit overnight. The optimum concentration of oil in the oil and water suspension was between approximately 1% and 7%. Ten milliliter aliquots of the oil-cell wall mixture were then transferred to sterile 1 liter beakers. Five hundred milliliters of sterile, phosphate buffered saline (0.05M sodium phosphate, pH 7.2, 9 g NaCl and 2 ml Tween-80 per liter of deionized water) were added to each 10 ml aliquot of oil and cell wall fraction. The mixture was homogenized by sonication and then transferred to sterile, capped bottles for storage at 4° C. Samples of the emulsion were examined under a coverslip with a light microscope to determine that the oil droplets were small and granular in appearance rather than clear with dark borders. Granular appearing droplets indicate that there has been proper adsorption of the cell wall to the oil carrier.

EXAMPLE VIII

Aluminum hydroxide (Reheis Chemical Co., Berkeley Heights, NJ) was prepared as an adjuvant and stabilizer to be added to the cell wall oil-in-water emulsion. Aluminum hydroxide was obtained as a 9.4% compressed gel and was hydrated to 1.3% aluminum oxide by the addition of deionized water, e.g., 138.3 g of compressed aluminum oxide gel is diluted to 1 liter. The gel was sterilized in an autoclave at 120° C. for 20 minutes before it was added to the cell wall suspension.

EXAMPLE IX

Bottles of the cell wall preparation in oil-in-water emulsion were pooled in a sterile mixing vessel, and 50 ml of 1.3% aluminum oxide, 50 ml of phosphate buffered saline and 0.1 grams of Thimerosal (Sigma Chemical Co., St. Louis, MO) were added to each liter of cell wall emulsion. Sterile Type 1 glass vials and plastic syringes were filled with 10 ml and 1.5 ml of the stabilized emulsion, respectively, under sterile laminar air flow using a Filamatic Vial Filler (National Instrument Co., Baltimore, MD). The vials and syringes were capped, sealed and stored at 4° C.

EXAMPLE X

The antiviral immunotherapeutic agent of the present invention was used to treat a herpesvirus infection in horses known as acute rhinopneumonitis.

Sixteen horses, all showing signs of acute rhinopneumonitis, were stabled individually. Every other horse was treated once with the antiviral immunotherapeutic agent of the present invention. The horses that were not treated with the antiviral immunotherapeutic agent of the present invention were treated with conventional therapy which consisted of antibiotics and analgesics. Nasal swabs were collected from two horses of each group and were used to inoculate cell cultures which were examined for specific herpesvirus, types 1 and 2, fluorescence by the method used by the National Animal Disease Laboratories in Ames, Iowa (see Carbery, E. A., et al., (1965) Technical Aspects of Tissue Culture Fluorescent Antibody Technique, *Proc. U.S. Livestock San. Asoc.*, 69th Annual Meeting, Lansing, MI, pages 487–500). The horses tested were positive for herpesvirus type 1 and negative for herpesvirus type 2. Control tests were negative.

All horses were examined at least once daily. Body temperatures and the clinical signs of nasal/ocular discharge, coughing and wheezing, inappetance, and general malaise were noted daily. Auscultation by stethoscope was used. Blood samples were collected from all of the horses just before they were treated. Blood samples were collected from the conventionally treated horses 3, 7, and 14 days later, and from the horses treated with the antiviral immunotherapeutic agent of the present invention 2, 5, 7, 14 and 21 days later. Undesirable side-effects were not observed in any of the horses treated with the antiviral immunotherapeutic agent of the present invention.

The clinical data have been summarized in Tables 1, 2 and 3. Table I shows the clinical data for the group of horses treated with the antiviral immunotherapeutic agent of the present invention.

TABLE I

| | | Horses treated with antiviral immunotherapeutic agent of the present invention | | | | |
|---|---|---|---|---|---|---|
| Sex | Age (years) | Initial temp. (F.°) | Duration treatment (days) | Days to Norm. Temp | Duration of Clinical Signs (days) | Days out of training |
| Colt | 2 | 103.6 | 1 | 2 | 2 | 7 |
| Geld. | 5 | 102.4 | 1 | 1 | 3 | 8 |
| Geld. | 4 | 101.6 | 1 | 1 | 2 | 4 |
| Geld. | 8 | 103.6 | 1 | 3 | 1 | 5 |
| Geld. | 5 | 102.0 | 1 | 1 | 2 | 5 |
| Filly | 3 | 104.4 | 1 | 3 | 2 | 6 |
| Filly | 4 | 103.6 | 1 | 2 | 3 | 9 |
| Mare | 5 | 102.2 | 1 | 1 | 1 | 7 |
| Mean | 4.5 | 102.9 | 1 | 1.8 | 2.0 | 6.4 |
| SD | 1.8 | 1.0 | 0 | 0.9 | 0.8 | 1.7 |

Table II summarizes the clinical data for the group of horses that were treated with conventional therapy.

TABLE II

| | | Horses Treated with Conventional Therapy | | | | |
|---|---|---|---|---|---|---|
| Sex | Age (years) | Initial temp. (F.°) | Duration treatment (days) | Days to Norm. Temp | Duration of Clinical Signs (days) | Days out of training |
| Colt | 2 | 103.4 | 11 | 7 | 38 | 40 |
| Horse | 5 | 102.4 | 5 | 3 | 29 | 32 |
| Geld. | 3 | 103.6 | 9 | 4 | 27 | 31 |
| Geld. | 4 | 104.0 | 7 | 8 | 22 | 22 |
| Geld. | 7 | 102.4 | 10 | 4 | 43 | 50 |
| Filly | 2 | 103.4 | 7 | 10 | 39 | 42 |
| Filly | 2 | 104.4 | 8 | 6 | 59 | 59 |
| Mare | 4 | 102.6 | 8 | 5 | 40 | 45 |
| Mean | 3.6 | 103.3 | 8.1 | 5.9 | 37.1 | 40.1 |
| SD | 1.0 | 0.8 | 1.9 | 2.4 | 11.5 | 11.7 |

Table III statistically compares the clinical data between the two groups of horses.

TABLE III

| | | | | | | |
|---|---|---|---|---|---|---|
| | | Pooled statistical comparison between the horses treated with the antiviral immunotherapeutic agent of the present invention and those treated with conventional therapy | | | | |
| Test | Age (years) | Initial temp. (F.°) | Duration treatment (days) | Days to Norm. Temp | Duration of Clinical Signs (days) | Days out of training |
| t | 0.989 | 0.794 | 10.690 | 4.525 | 8.634 | 8.073 |
| P | NS | NS | 0.0001 | 0.0001 | 0.0001 | 0.0001 |

There was no difference in the distribution of sex and age between the two treatment groups. The difference in clinical data between the immunotherapy and conventional groups was highly significant (P≦0.0001). The duration of treatment was 1 day for the immunotherapeutic agent versus 8 days for conventional agents, and body temperatures returned to normal in 2 days for the immunotherapeutic agent versus 8 days for the conventional therapy. The duration of clinical signs was 2 days for the immunotherapeutic agent versus 37 days for the conventional therapy. The time out of training was 6 days for the horses treated with the antiviral immunotherapeutic agent vs 40 days for the horses treated with conventional therapy.

No differences were found between the two treatment groups in red blood cell count, PCV, hemoglobin, MCV, MCH, MCHC, glucose, blood urea nitrogen, creatinine, T4, amylase, calcium, phosphorous, sodium, potassium, alkaline phosphatase, γ-glutamyl transpeptidase, lactic dehydrogenase or albumin. The values for each parameter were consistently in the normal ranges for both groups of animals. The horses were evaluated for development of autoimmunity by examining them for circulating antinuclear antibodies. None were detected.

Several blood parameters, especially the acute phase proteins, were concordant with the clinical data, and they objectively confirmed the subjective data by demonstrating that the damage caused by herpesviruses in the respiratory tract had undergone faster resolution in horses treated with the antiviral immunotherapeutic agent of the present invention than in horses treated conventionally. Original values, obtained prior to treatment, were used as the "control" values for subsequent measurements in each horse. This allowed inferences to be made with the paired t statistic. Since there is less variation of a parameter in an individual horse than there is among all of the horses, the paired t test is the preferred statistical test for determining significant differences. The data were also analyzed with pooled t tests. The inferences obtained with this test were the same as the paired t tests although they were less pronounced and were not significant as early in the experiment as when the paired t test was used.

Electrophoretic analysis of serum proteins was done to evaluate the effect of the treatment on the response of the acute phase proteins. The α-1 globulin fraction was elevated in both groups at the beginning of therapy and decreased to normal levels in the immunotheraphy group within one week, but it continued to increase in the conventionally treated group. The α-1 antitrypsin peak which appears in the α-1 fraction during pulmonary damage and correlates better than any other parameter with the pulmonary damage, was evident in each electrophoretogram when treatment was begun. It was absent from the electrophoretograms of the immunotherapy group two days after treatment with the immunotherapeutic but it persisted in electrophoretograms of the horses treated conventionally. The α-2 globulin fraction was initially in the normal range, where it remained in the immunotherapy group, but it continued to rise to higher than normal levels in the conventionally treated horses and fell with time in the horses treated with the antiviral immunotherapeutic agent of the present invention, although it was always in the normal range. The gamma globulin fraction was unchanged in the conventionally treated horses, but it rose steadily in the horses treated with the immunotherapeutic and was higher than normal after the first week. Concordant with the rise in the γ fraction, total serum IgM levels were elevated and continued to rise in the immunotherapy group. Leukopenia was present initially and increased to normal levels within a week in both groups. Circulating monocytes (phagocytic cells) were initially high in both groups, but they declined to normal levels in two days following immunotherapy and continued to rise in the horses treated conventionally. Taken together, the clinicopathologic data correlated with the clinical observations, and they clearly showed that immunotherapy effectively altered the course of the disease. Rapid declines in α-1 anitrypsin and the relative numbers of circulating monocytes were clear indications that immunotherapy prevented the development of significant pulmonary damage. Consequently, the horses were ready for normal exercise in one week whereas the conventionally treated horses were not ready for several more weeks while the pulmonary damage was being resolved.

Thus, the antiviral immunotherapeutic agent of the present invention significantly alters the course of infection, and damage to the respiratory tissues is greatly reduced.

It should be understood, of course, that the foregoing relates only to a preferred embodiment of the present invention and that numerous modifications or alterations may be made therein without departing from the spirit and the scope of the invention as set forth in the appended claims.

I claim:

1. A method of treating a viral infection in animals and humans comprising the step of injecting an animal or human with an effective amount of a deproteinized bacterial cell wall suspension in an oil and water emulsion, wherein the bacterial cell wall suspension is derived from bacteria being selected from the group consisting of Mycobacterium species, Corynebacterium species and Nocardia species.

2. The method of claim 1 wherein the Mycobacterium species is *Mycobacterium phlei.*

3. A method for protecting an animal or human against a viral infection comprising injecting an effective amount of an antiviral immunotherapeutic agent comprising an effective amount of a deproteinized bacterial cell wall suspension from which nucleic acids and lipids have been extracted by treatment with a detergent and phenol, in an oil and water emulsion, said oil being present in the oil and water emulsion at a concentration of between approximately 1% and 7%, said bacterial cell wall being derived from bacteria selected from the group consisting of Mycobacterium species, Corynebacterium species and Nocardia species, and said deproteinized bacterial cell wall retaining trehalose dimycolate therein.

* * * * *